US00PP27164P3

(12) United States Plant Patent
Anderson et al.

(10) Patent No.: US PP27,164 P3
(45) Date of Patent: Sep. 20, 2016

(54) RED DELICIOUS APPLE TREE NAMED 'WESTFRESH'

(50) Latin Name: ***Malus domestica* Borkh**
Varietal Denomination: Westfresh

(71) Applicant: WestFresh LLC, Royal City, WA (US)

(72) Inventors: Beau J. Anderson, East Wenatchee, WA (US); Jesse J. Anderson, East Wenatchee, WA (US)

(73) Assignee: WestFresh LLC, Royal City, WA (US)

( * ) Notice: Subject to any disclaimer, the term of this patent is extended or adjusted under 35 U.S.C. 154(b) by 137 days.

(21) Appl. No.: 13/998,832

(22) Filed: Dec. 12, 2013

(65) Prior Publication Data

US 2015/0173265 P1 Jun. 18, 2015

(51) Int. Cl.
*A01H 5/08* (2006.01)

(52) U.S. Cl.
USPC ..... Plt./171

(58) Field of Classification Search
USPC ..... Plt./156, 161, 171
See application file for complete search history.

(56) References Cited

PUBLICATIONS

Letter from inventor Beau J. Anderson to the United States Patent and Trademark Office, dated Mar. 24, 2014.

*Primary Examiner* — Susan McCormick Ewoldt
*Assistant Examiner* — Karen Redden
(74) *Attorney, Agent, or Firm* — Klarquist Sparkman, LLP

(57) ABSTRACT

This apple is unique in its combination of color, red stripe, and excellent long-term storage, which results in improved pack-out.

3 Drawing Sheets

Latin name of the genus and species of the plant claimed: *Malus domestica* Borkh.

Variety denomination: 'Westfresh'.

BACKGROUND OF THE INVENTION

The present invention relates to a new and distinct variety of red delicious apple tree named 'Westfresh'. The new tree resulted from the discovery in the early '90s, by one of the inventors of a limb sport mutation on an 'Oregon Spur II' (expired U.S. Plant Pat. No. 4,819) growing in a cultivated area of an orchard in East Wenatchee, Wash.

BRIEF SUMMARY OF THE INVENTION

The 'Westfresh' variety is distinguished from other apple varieties due to the following unique combination of characteristics:

A large, very elongated Red Delicious; very dark red in color with dark stripes. 'Westfresh' Red Delicious exhibits excellent long-term storage evidenced by high pack-out rates. Pack-out refers to the percentage of apples that are of a high quality following long-term cold storage. After 10 months of storage in a controlled atmosphere environment (33 to 34 degrees Fahrenheit and with oxygen in the environment replaced by nitrogen), eighty percent or more of the apples are of high quality in that there has been an insignificant reduction in pressure and sugars in the apples. Thus, if twenty five boxes of apples from trees of my new variety are placed into cold storage, enough high quality apples remain following long-term cold storage to fill twenty or more (often 22 or more) boxes.

The 'Westfresh' Red Delicious apple tree is also very resistant to scab, powdery mildew and fireblight.

Asexual reproduction of this new variety was performed by grafting in Rock Island, Wash. onto M III (unpatented) rootstock and has shown that the foregoing characteristics come true to type.

The following detailed description is based upon observations of the original limb sport, approximately 18 years old, and five-year-old asexually propagated progeny.

The original limb sport and progeny have been observed in a cultivated orchard in East Wenatchee and Rock Island, Wash. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to Munsell Book of Color, Kollmorgen Instruments Corp. 405 Little Britain Road, New Windsor, N.Y. 12553.

Figure 1:
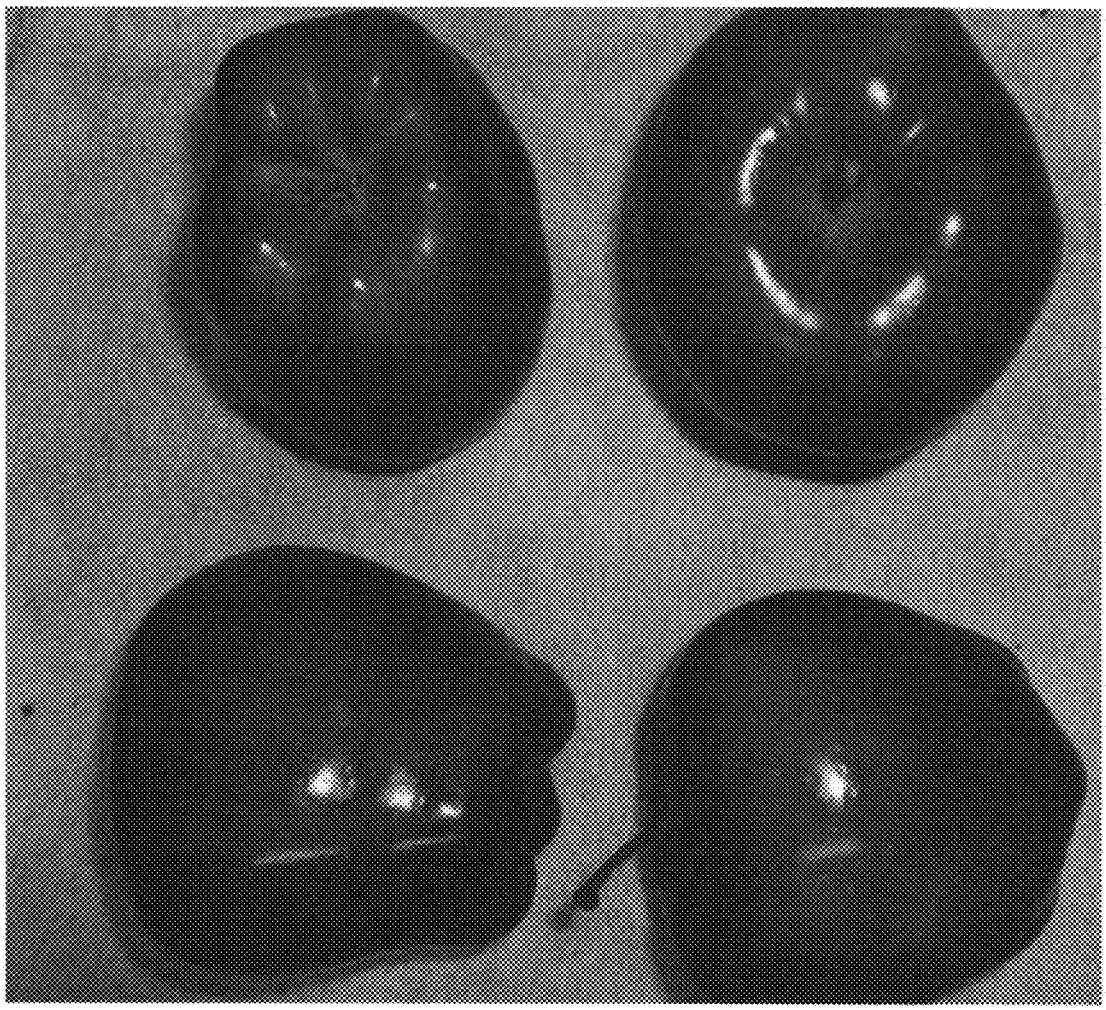
FIG. 1 is a photograph of apples from trees of the 'Westfresh' variety taken on Sep. 17, 2012. The apples were grown on 5-year-old trees in Rock Island, Wash.
Figure 2:
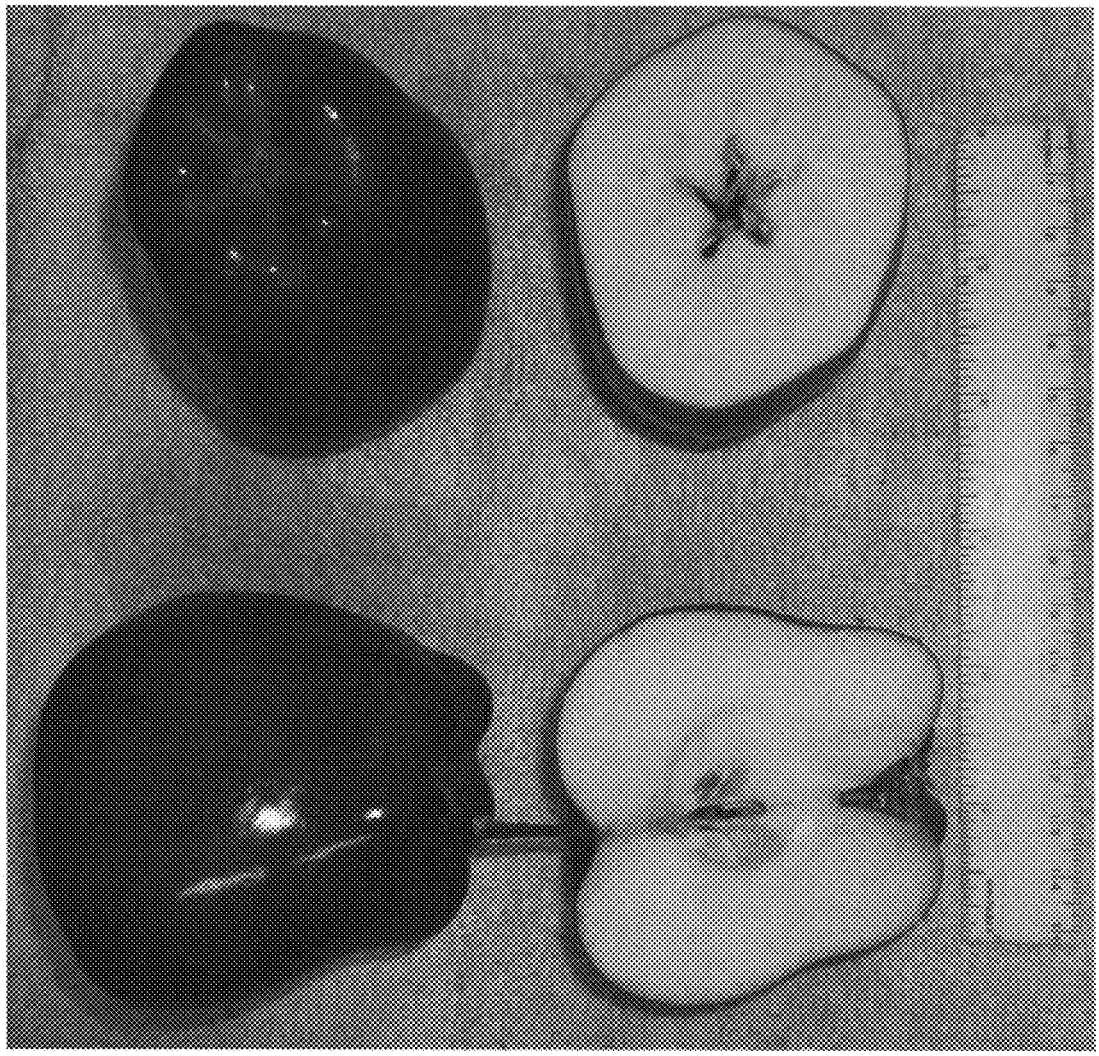
FIG. 2 is a photograph of cross-sections of representative apples from trees of the 'Westfresh' variety taken at the same time as the photograph of FIG. 1.
Figure 3:
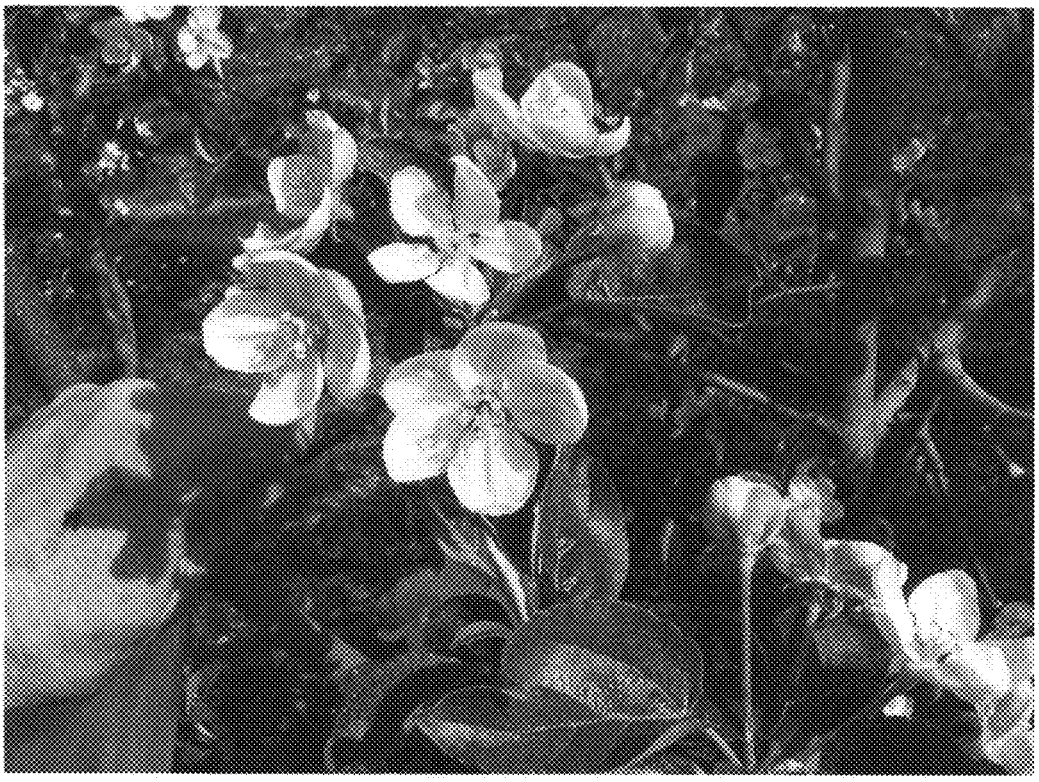
FIG. 3 is a photograph of a limb of a 5-year-old 'Westfresh' tree with flowers.

The colors of an illustration of this type may vary with lighting and other conditions and, therefore, color characteristics of this new variety should be determined with reference to the observations described herein, rather than from these illustrations alone.

DETAILED DESCRIPTION

The following detailed description of the 'Westfresh' variety is based on observations of a 5-year-old tree of my new variety and of the original limb sport. The observed progeny were growing on M 111 rootstock in an orchard in Rock Island, Wash.

Scientific name: *Malus domestica* Borkh.

Parentage: Limb sport of an 'Oregon Spur II' apple tree.

Tree:

*Vigor*.—Very vigorous.

*Habit*.—Spur type, compact and spreading.

*Height*.—Typically: 10' for 5-year-old trees.

*Width*.—Typically: 8' for 5-year-old trees.

*Trunk*.—Diameter of 5-year-old trees is 7 inches measured at 12 inches above graft union.

*Trunk bark texture*.—Smooth with shallow furrows.

*Trunk bark color*.—Light Gray (7.5 Y 7/2).

*Trunk lenticels*.—Color: Charcoal Gray (7.5 Y 3/2).

*Shape*.—Roundish, irregular.

*Size*.—1/16"×3/16".

*Branch length*.—One-year-old branches: Typically: 18-24"; diameter 1/4" to 3/8".

*Crotch angle of branches*.—Typically: 60°, but increases when branches are loaded with fruit.

*Bearing*.—On spurs.

*Branch color*.—One-year-old branches are Reddish Brown (2.5 YR 3/4).

*Branch pubescence*.—Light at base, increasing in density towards the tip.

*Branch lenticels*.—Density approximately 15 per square inch; on 1-year-old branch, typical lenticels are mostly long oval, and measured about 1/64" in diameter and 1/32" long.

*Lenticel color*.—Light Tan (7.5 YR 7/4).

*Internode length*.—Typical internode length is about 3/4" to 1 1/4" on one-year-old branches.

*Bearing*.—Annual, like 'Oregon Spur II'.

*Winter hardiness*.—Hardy in Rock Island, Wash.; hardiness Zone 4.

*Disease resistance*.—Similar to 'Oregon Spur II'.

Leaves: Measurements were obtained from ten typical leaves picked Jul. 25, 2012 in Rock Island, Wash.

*Texture*.—Leathery.

*Sheen*.—Upper surface dull to slightly glossy; lower surface dull.

*Length*.—About 2 1/2 inches to about 3 1/2 inches, averaging about 2 3/4 inches.

*Width*.—1 1/2 inches to 1 9/16 inches.

*Thickness*.—About 1/128 of an inch.

*Petiole*.—About 1 to 1 1/4 inches long; and about 1/16 of an inch in diameter; color; Light Green (5 GY 7/4).

*Margin*.—Crenate.

*Overall shape*.—Elongated oval.

*Tip shape*.—Acuminate.

*Base shape*.—Acute to obtuse.

*Stipules*.—Mostly lacking, except at branch tip; opposite in arrangement; Light Green (5 GY 8/4) in color; shape is very narrow; length is about 5/16 of an inch long; width is about 1/16 of an inch.

*Leaf color*.—

*Upper leaf surface*.—Dark Green (5 GY 3/6).

*Lower leaf surface*.—Gray Green (5 GY 3/4).

*Venation pattern*.—Alternate.

*Vein upper surface*.—Medium Green (5 GY 6/6).

*Vein lower surface*.—Light Green (5 GY 7/4).

*Pubescence*.—Upper surface glabrous.

*Lower surface pubescence*.—Light on lower leaf surface.

*Color*.—Very Light Green (5 GY 9/2).

Flowers:

*Buds*.—Quantity: 3 to 6 buds per spur.

*Bud size*.—3/8 to 3/16 of an inch in diameter.

*Flower size when open*.—1 1/2 to 2 1/4 inches in diameter.

*Color*.—Tight bud: Deep Rose (7.5 RP 4/10), fully open flower: Very Light Pink (7.5 RP 9/2) to pure white with more Medium Rose (7.5 RP 6/8) along veins of petals.

*Pedicel*.—Light Gray Green (5 GY 7/4); size about 1 inch long by 1/16 inch in diameter.

*Petals*.—5 petals per flower; petal size about 1 inch long by 1/2 an inch wide; arrangement: overlapping slightly.

*Sepals*.—Quantity per flower: 5; shape: somewhat recurving; overall shape is deltoid, the tip is acuminate, the base is tapering in shape; length is 3/4 inch; width is about 3/16"; color is Medium Green (5 GY 7/4).

*Stamens*.—Number: 10-12.

*Anthers*.—Quantity per flower: 10-12: renal shaped; width about 1/16 inch, length about 3/32 inch; pollen color: Bright Yellow (5 Y 8/12).

*Filaments*.—Length 3/8 inch; color: Cream (7.5 Y 9/4).

*Pistil*.—Length: 5/16".

*Styles*.—Number: 5; form: joined at base; average length about 3/8 inch; color: Cream (7.5 Y 9/4).

*Ovary*.—Length: 3/16 inch; color: Light Green (5GY 7/4), pubescent.

*Stigma*.—Shape: clubbed; color: Medium Brownish Yellow (2.5 Y 6/10).

*Peduncle*.—Length about 1/4" to 3/8"; color: Dull Green (5 GY 7/4); finely pubescent; short, identical to pubescence on petiole.

*Pollination requirement*.—Expected to be diploid, self-sterile.

Bloom season: Initial bloom was observed on Apr. 30, 2012 in Rock Island, Wash.

*Full bloom date*.—May 5, 2012 in Rock Island, Wash.

Fruit: Observations from a limited number of typical fruit in the laboratory. Maturity when described: Sep. 17, 2012, at Rock Island, Wash.

*Size*.—Medium-large, 3 to 3 1/2 inches long and from 2 3/4 to 2 7/8 inches diameter at the widest point.

*Position of maximum diameter*.—Just above the equator.

*Form*.—Long conic.

*Ribbing*.—Moderately ribbed.

*Stem cavity*.—1 1/2 inches wide and 1/2 inch deep.

*Stem*.—Medium thickness; 1 inch long and 1/18 inch in diameter, stem color: Reddish Brown (2.5 R 3/4).

*Crowning at calyx end*.—Very prominent.

*Aperture of the eye*.—Closed to partially open.

*Sepals at eye basin*.—Surface texture: Downy; color: Dark Gray Green (2.5 Y 3/4).

*Eye basin*.—About 3/8 inch deep and about 1 1/2 inches wide; pubescence observed as present. Shape of eye-basin: Strongly furrowed, with 5 prominent points.

*Skin*.—Intensity of color is dark and prominently striped, bloom of skin is present. Greasiness is absent.

*Skin lenticels*.—Generally prominent; numbers are about 15 per square inch appearing at the stem end of the fruit, and about 30 per square inch appearing at the calyx end of the fruit; surface texture: perfectly smooth; Cream color (10 Y 8/4). Size of lenticels is variable from 1/128 of an inch to 1/32 of an inch.

*Core*.—Generally average in size, from 3/4 to 1 inch in diameter, 1 inch in length. Core position is basal clasping.

*Locules*.—Narrow, partially open; size of locule: 7/8 of an inch in length by 1/8 of an inch in width.

*Tube*.—Shape: cone.

*Stamen position*.—Generally median.

*Axis position*.—Considered closed.

*Seed*.—Number: Generally 6, occasionally 10; shape—Acuminate; length about 5/16 of an inch; width about 3/16 of an inch. Color is Dark Brown (5 YR 2/4).

*Fruit flesh*.—Generally firm, crisp and juicy. Color is Light Cream (7.5 Y 9/2).

*Fruit aroma*.—Considered mild and typical for the species.

*Starch*.—Generally about 4 out of 6 starch level in iodine (at prime maturity). Acids are 0.4%.

*Fruit pressure*.—18.

*Soluble solids*.—13.

*Skin color*.—Overall dark red with deep red pronounced stripe. Overcolor of Skin: Deep Purplish Red (10 RP 3/6) over about 90 to 100% of the surface. Ground color of the skin: Reddish Yellow (5 R 6/8). Color of stripe: Deep Red (7.5 R 3/8). Russetting: Absent.

*Fruit weight*.—Average weight of representative apples is about one-half pound.

*Productivity*.—In Rock Island, Wash.; approximately 1680 bushels per acre.

*Cold storage*.—Good condition when in cold storage for 100+ days at 31° F.; it will keep much longer in a controlled atmosphere (33 to 34° F., oxygen replaced with nitrogen).

*Market use*.—Dessert.

*Harvest date*.—October 23rd to 31st in Rock Island, Wash. in 2012.

*Winter hardiness*.—Observed in Rock Island, Wash.; hardiness zone 7a. Range of winter hardiness zones unknown.

*Drought/heat tolerance*.—Not observed except that drought and heat tolerance in Rock Island, Wash. appears to be like that of other red delicious varieties growing in Rock Island, Wash.

Comparative Data to Other Varieties (e.g., Harvest Date)

TABLE 1

Harvest date for 'Westfresh' and other Red Delicious Varieties in Rock Island, Washington.

| Variety (*) | Harvest Dates |
|---|---|
| 'Flinn' (unpatented) | Oct. 20, 2012 |
| 'Bisbee' (U.S. Expired Plant Pat. No. 1565) | Oct. 30, 2012 |
| 'Westfresh' | Oct. 23, 2012 |

((*) Comparison Varieties and patent status)

'Westfresh' differs from 'Oregon Spur II', in that 'Westfresh' has apples with very dark red color with dark stripes and by their excellent long term storage in a controlled environment.

'Westfresh' apples are a darker red than apples of the 'Burchinal Red Delicious' variety (U.S. Plant Pat. No. 14,757). In addition, 'Westfresh' apples have a deep dark stripe.

We claim:

1. A new and distinct variety of apple tree as herein shown and described.

* * * * *